US00PP37111P2

(12) United States Plant Patent
Neu

(10) Patent No.: US PP37,111 P2
(45) Date of Patent: Nov. 25, 2025

(54) ***PELARGONIUM* PLANT NAMED 'KLEPZ24874'**

(50) Latin Name: *Pelargonium zonale*
Varietal Denomination: KLEPZ24874

(71) Applicant: KLEMM + SOHN GMBH & CO. KG, Stuttgart (DE)

(72) Inventor: Nina Neu, Weissach im Tal (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/202,503

(22) Filed: May 8, 2025

(30) Foreign Application Priority Data

May 13, 2024 (CH) ..... 24-3624

(51) Int. Cl.
*A01H 5/02* (2018.01)
*A01H 6/42* (2018.01)

(52) U.S. Cl.
USPC ..... Plt./330

(58) Field of Classification Search
USPC ..... Plt./330
See application file for complete search history.

(56) References Cited

U.S. PATENT DOCUMENTS

PP30,335 P2 4/2019 Klemm et al.
PP30,460 P3 4/2019 Klemm et al.
PP35,133 P2 * 4/2023 Snijder ..... A01H 6/425 Plt./330

* cited by examiner

*Primary Examiner* — Susan Mccormick Ewoldt
(74) *Attorney, Agent, or Firm* — Weatherly IP Solutions, LLC; James M. Weatherly

(57) ABSTRACT

A new *Pelargonium* plant particularly distinguished by orange-red flowers, and leaves with a medium zonation; is disclosed.

1 Drawing Sheet

Genus and species: *Pelargonium zonale*.
Variety denomination: 'KLEPZ24874'.

CROSS REFERENCE TO RELATED APPLICATION

This patent application claims the benefit of priority from Plant Variety Protection Certificate No. 24-3624 as filed on May 13, 2024, in Switzerland, the contents of which are incorporated herein by reference for all they teach and disclose.

BACKGROUND OF THE NEW PLANT

The present invention comprises a new and distinct variety of *Pelargonium*, botanically known as *Pelargonium zonale* and hereinafter referred to by the variety name 'KLEPZ24874'. 'KLEPZ24874' originated from a controlled cross in July 2019 in Juja, Kenya between the female *Pelargonium* variety 'KLEPZ17484' (U.S. Plant Pat. No. 30,335) and the male *Pelargonium* variety 'KLEPZ17154' (U.S. Plant Pat. No. 30,460).

Seeds from the controlled cross were obtained, sown and plants were grown for evaluation. A single plant was selected in June 2020 and subsequently named 'KLEPZ24874'. In July 2020, 'KLEPZ24874' was first vegetatively propagated by vegetative stem cuttings in Stuttgart, Germany. 'KLEPZ24874' was found to reproduce true to type in successive generations of asexual propagation via stem cuttings in Stuttgart, Germany.

SUMMARY

The following are the most outstanding and distinguishing characteristics of this new variety when grown under normal horticultural practices in Stuttgart, Germany.

1. Orange-red flowers; and
2. Leaves with a medium zonation.

DESCRIPTION OF THE PHOTOGRAPH

This new *Pelargonium* plant is illustrated by the accompanying photograph which shows an overall view of the plant in a pot. The photograph is of an approximately 14-week-old plant grown indoors in Stuttgart, Germany. The photograph was taken indoors in Stuttgart, Germany in May 2023. The colors shown are as true as can be reasonably obtained by conventional photographic procedures.

DESCRIPTION OF THE NEW VARIETY

The following detailed descriptions set forth the distinctive characteristics of 'KLEPZ24874'. Data was collected on 16-week-old plants in Stuttgart, Germany grown under greenhouse conditions in April 2025. Color references are to The R.H.S. Colour Chart of The Royal Horticultural Society of London (R.H.S.), 5$^{th}$ edition (2007).

Classification:
*Family*.—Geraniaceae.
*Botanical*.—*Pelargonium zonale*.
*Common*.—*Pelargonium*.
*Designation*.—'KLEPZ24874'.

Parentage:
*Female parent*.—'KLEPZ17484' (U.S. Plant Pat. No. 30,335).
*Male parent*.—'KLEPZ17154' (U.S. Plant Pat. No. 30,460).

Plant:
*Form*.—Bushy.
*Habit*.—Mounding.
*Height* (*from top of soil*).—22.0 cm.
*Width* (*horizontal plant diameter*).—25.0 cm.
*Natural flowering season*.—March to October.
*Propagation type*.—Vegetative by stem cuttings.
*Time to produce a finished flowering plant*.—12 weeks.
*Time to initiate and develop roots*.—4 weeks.
*Root description*.—Fine, dense, white, 158A.
*Flower type*.—Zygomorphic.

Stems:
*Quantity of stems per plant*.—3 to 4.
*Color*.—146B.
*Surface texture*.—Pubescent.
*Stem form*.—Round.
*Diameter*.—0.8 cm.
*Length*.—7.5 cm to 10.0 cm.
*Internode length*.—2.0 cm.
*Anthocyanin*.—None observed.

Leaves:
*Arrangement*.—Alternate.
*Shape*.—Reniform.
*Apex*.—Round.
*Base*.—Closed.
*Margin*.—Crenate.
*Surface texture both surfaces*.—Pubescent.
*Length*.—6.3 cm.
*Width*.—5.5 cm.
*Color*.—Upper surface: N137A. Lower surface: 137C.
*Zonation*.—Medium, distance from base 2.0 cm, distance from margin 1.0 cm.
*Zonation color*.—N200A.
*Depth of sinus*.—2.0 cm.
*Petiole*.—Length: 5.0 cm. Diameter: 0.3 cm. Color: 146B. Strength: Medium.
*Venation pattern*.—Palmate.
*Venation color*.—Upper surface: N137A. Lower surface: 146B.

Inflorescence:
*Lastingness of flowers on the plant*.—6 to 8 days.
*Umbels*.—Quantity of umbels per plant: 5 to 6. Length: 6.0 cm. Diameter: 9.0 cm.
*Individual florets of the umbel*.—Quantity of florets per umbel: 30 to 35. Depth: 2.0 cm. Diameter: 4.5 cm.
*Fragrance*.—Absent.

Flower buds:
*Cluster shape*.—Round.
*Cluster size*.—Length: 1.3 cm. Width: 1.5 cm.
*Surface texture*.—Pubescent.
*Bud*.—Height: 1.1 cm. Width: 0.6 cm. Shape: Round. Apex: Acute. Base: Obtuse. Margin: Entire. Color: 146B.

Petals:
*Quantity per flower*.—8 to 9.
*Shape*.—Spatulate.
*Apex*.—Round.
*Base*.—Obtuse.
*Margin*.—Entire.
Length.—3.0 cm.
Width.—2.5 cm.
*Surface texture*.—Upper surface: Smooth. Lower surface: Smooth.
*Color of lobes*.—Upper lobes: Upper surface: 44B. Lower surface: N30A. Lower lobes: Upper surface: 44B. Lower surface: N30A.
*Markings*.—Absent.

Petaloids:
*Quantity per flower*.—1 to 3.
*Shape*.—Crippled deformed spatulate.
*Apex*.—Round.
*Base*.—Obtuse.
*Margin*.—Entire.
*Length*.—1.0 cm to 2.0 cm.
*Width*.—0.5 to 1.0 cm.
*Surface texture*.—Upper surface: Smooth. Lower surface: Smooth.
*Color*.—Upper surface: 44B. Lower surface: N30A.

Sepals:
*Number per flower*.—5.
*Shape*.—Elliptic.
*Apex*.—Acute.
*Base*.—Obtuse.
*Margin*.—Entire.
*Surface texture*.—Upper surface: Smooth. Lower surface: Pubescent.
*Color*.—Upper surface: 246B at tip, 184A at base. Lower surface: 246B at tip, 184A at base.
*Length*.—1.3 cm.
*Width*.—0.3 cm.

Pedicel:
*Length*.—2.2 cm.
*Diameter*.—0.2 cm.
*Color*.—187A.
*Surface texture*.—Pubescent.
*Strength*.—Medium.

Peduncle:
*Length*.—12.5 cm.
*Diameter*.—0.5 cm.
*Color*.—187A.
*Texture*.—Pubescent.
*Strength*.—Strong.

Reproductive organs:
*Stamens*.—Quantity per flower: 5 to 7. Anther length: 0.2 cm. Filament length: 0.4 cm. Filament color: NN155C at base, 43A at tip. Pollen amount: Medium. Pollen color: 33B.
*Pistils*.—Number: 1. Stigma color: 46A. Style length: 0.2 cm. Style color: 46A. Ovary arrangement: Central. Ovary color: 46A. Ovary diameter: 0.2 cm. Ovary length: 0.5 cm. Ovary Texture: Pubescent.

Fruit and seed set: None observed.

Disease and pest/insect resistance: None observed.

COMPARISON WITH PARENTAL LINES AND KNOWN VARIETY

'KLEPZ24874' is distinguished from its parents as described in Table 1.

TABLE 1

| Comparison with Parental Lines | | | |
|---|---|---|---|
| Characteristic | 'KLEPZ24874' | Female parent | Male parent |
| Strength of Leaf Zonation | Medium | Very strong | Weak |
| Flower Color | Orange red | Purple red | Dark red |

'KLEPZ24874' can be compared to the commercial variety Dolce Vita Mylena (patent status unknown). Differences between the two varieties are described in Table 2:

TABLE 2

| Comparison with Similar Variety | | |
|---|---|---|
| Characteristic | 'KLEPZ24874' | Dolce Vita Mylena |
| Strength of leaf zonation | Medium | Very strong |

I claim:

1. A new and distinct variety of *Pelargonium* plant named 'KLEPZ24874' as illustrated and described herein.

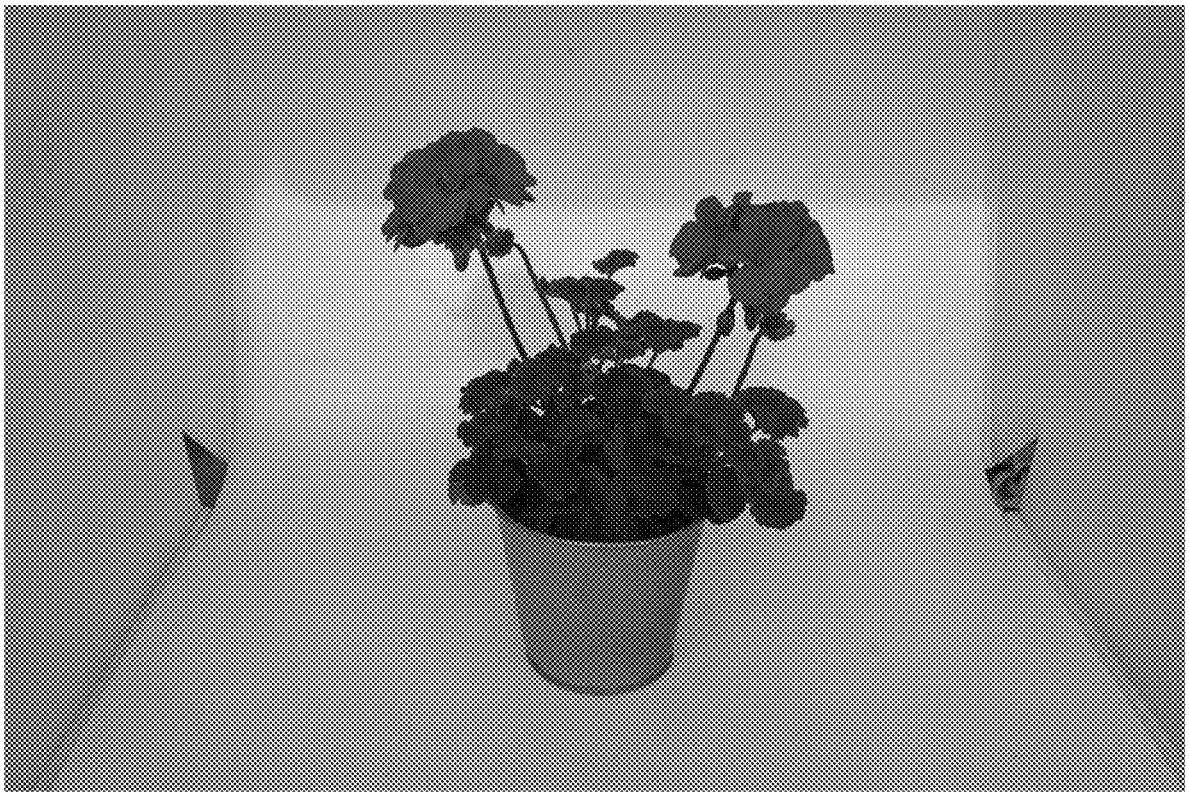

* * * * *